US012778435B2

(12) United States Patent
Koivisto et al.

(10) Patent No.: US 12,778,435 B2
(45) Date of Patent: Nov. 3, 2026

(54) APPARATUS AND A METHOD FOR MEASURING JUGULAR VEIN PRESSURE WAVEFORM

(71) Applicant: Precordior Oy, Turku (FI)

(72) Inventors: Tero Koivisto, Turku (FI); Tuukka Panula, Turku (FI); Matti Kaisti, Turku (FI); Mikko Pänkäälä, Turku (FI)

(73) Assignee: PRECORDIOR OY, Turku (FI)

(*) Notice: Subject to any disclaimer, the term of this patent is extended or adjusted under 35 U.S.C. 154(b) by 703 days.

(21) Appl. No.: 18/253,569

(22) PCT Filed: Nov. 20, 2021

(86) PCT No.: PCT/FI2021/050796
§ 371 (c)(1),
(2) Date: May 18, 2023

(87) PCT Pub. No.: WO2022/112651
PCT Pub. Date: Jun. 2, 2022

(65) Prior Publication Data
US 2024/0008754 A1 Jan. 11, 2024

(30) Foreign Application Priority Data
Nov. 24, 2020 (FI) ..................................... 20206195

(51) Int. Cl.
*A61B 5/021* (2006.01)
*A61B 5/00* (2006.01)
(Continued)

(52) U.S. Cl.
CPC ........ *A61B 5/02141* (2013.01); *A61B 5/0002* (2013.01); *A61B 5/02125* (2013.01); *A61B 5/318* (2021.01); *A61B 5/6822* (2013.01)

(58) Field of Classification Search
CPC .............. A61B 5/0002; A61B 5/02116; A61B 5/02125; A61B 5/02133; A61B 5/02141;
(Continued)

(56) References Cited

U.S. PATENT DOCUMENTS 5,908,027 A 6/1999 Butterfield et al.
2008/0294070 A1 11/2008 Kinori
(Continued)

FOREIGN PATENT DOCUMENTS

CN 110215198 A 9/2019
EP 4537746 A2 4/2025
(Continued)

OTHER PUBLICATIONS

U.A. Baumann et al., "Estimation of central venous pressure by ultrasound," Resuscitation, vol. 64, 2005, pp. 193-199.
(Continued)

*Primary Examiner* — Benjamin J Klein
*Assistant Examiner* — Vynn V Huh
(74) *Attorney, Agent, or Firm* — NIXON & VANDERHYE

(57) ABSTRACT

An apparatus for measuring a jugular vein pressure waveform includes a rotation sensor configured to produce a measurement signal when being against a skin of an individual and in a movement sensing relation with a jugular vein of the individual. The apparatus includes a processing system configured to receive the measurement signal and produce a waveform of a motion of the skin in a direction perpendicular to the skin based on the measurement signal indicative of rotation of the rotation sensor, where the waveform of the motion of the skin is indicative of the jugular vein pressure waveform. The rotation sensor that measures rotation is more insensitive to movements not
(Continued)

related to variation of the jugular vein pressure than for example an acceleration sensor.

17 Claims, 3 Drawing Sheets

(51) Int. Cl.
*A61B 5/11* (2006.01)
*A61B 5/318* (2021.01)

(58) Field of Classification Search
CPC ..... A61B 5/1102; A61B 5/318; A61B 5/6822; A61B 5/6832
See application file for complete search history.

(56) References Cited

U.S. PATENT DOCUMENTS

| | | | | |
|---|---|---|---|---|
| 2010/0094141 | A1 | 4/2010 | Puswella | |
| 2012/0101344 | A1 | 4/2012 | Desjardins et al. | |
| 2012/0136240 | A1 | 5/2012 | Pranevicius et al. | |
| 2012/0197118 | A1 | 8/2012 | Lisiecki et al. | |
| 2016/0220152 | A1* | 8/2016 | Meriheinä | A61B 5/7246 |
| 2017/0027457 | A1* | 2/2017 | Wagle | A61B 5/02028 |
| 2017/0296119 | A1 | 10/2017 | DeBusschere | |
| 2018/0000356 | A1 | 1/2018 | Ajima | |
| 2018/0146871 | A1 | 5/2018 | Ajima | |
| 2018/0184977 | A1 | 7/2018 | Nahmias et al. | |
| 2019/0254542 | A1 | 8/2019 | Wagle et al. | |
| 2020/0008684 | A1 | 1/2020 | Feinberg | |
| 2021/0259560 | A1 | 8/2021 | Venkatraman et al. | |
| 2021/0407276 | A1 | 12/2021 | Ajima | |
| 2022/0071561 | A1 | 3/2022 | Ajima | |
| 2022/0248993 | A1* | 8/2022 | Dixon | A61B 5/14553 |

FOREIGN PATENT DOCUMENTS

| | | | |
|---|---|---|---|
| EP | 4670631 | A2 | 12/2025 |
| JP | 2011229615 | A | 11/2011 |
| JP | 2016530049 | A | 9/2016 |
| JP | 2019063583 | A | 4/2019 |
| JP | 2019076120 | A | 5/2019 |
| KR | 20180084043 | A | 7/2018 |
| WO | 2008098353 | A1 | 8/2008 |
| WO | 2017060569 | A1 | 4/2017 |
| WO | 2018161159 | A1 | 9/2018 |
| WO | WO-2022112651 | A1 | 6/2022 |
| WO | WO-2023222944 | A1 | 11/2023 |

OTHER PUBLICATIONS

Finnish Search Report for FI 20206195 dated Jul. 6, 2021, 2 pages.
International Search Report and Written Opinion of the ISA for PCT/FI2021/050796 mailed Feb. 16, 2022, 15 pages.
Marc Foster et al., "Inertial Measurement Based Heart and Respiration Rate Estimation of Dogs During Sleep for Welfare Monitoring", Nov. 10, 2020, 4th International Conference on Big Data Research (ICBDR), 6 pages, XP058587058.
S. Bagyaraj et al., "Acquisition of Jugular Venous Pulse Waveform by a Non-invasive Technique", Recent Advances in Mechanical Engineering, Jan. 25, 2020, pp. 343-352.
EP Serial No. 251604463.3 Extended European Search Report dated May 23, 2025.
TW110143358 Office Action with Search Report dated Feb. 4, 2025, and an English translation.
PCT/FI2021/050796 International Preliminary Report on Patentability dated Jun. 8, 2023.
PCT/FI2023/050253 International Search Report and Written Opinion dated Aug. 18, 2023.
PCT/FI2023/050253 International Preliminary Report on Patentability dated Nov. 7, 2024.
Office Action, issued in Japanese Patent Application No. 2023-530969 dated Mar. 3, 2026.
Office Action, issued in Taiwanese Patent Application No. 114143719 dated Jan. 6, 2026.
Office Action, issued in Korean Patent Application No. 10-2023-7016042 dated Jun. 22, 2026.
Office Action, issued in Australian Patent Application No. 2021386762 dated Jun. 30, 2026.

* cited by examiner

APPARATUS AND A METHOD FOR MEASURING JUGULAR VEIN PRESSURE WAVEFORM

CROSS-REFERENCE TO RELATED APPLICATIONS

This application is the U.S. national phase of International Application No. PCT/FI2021/050796 filed Nov. 20, 2021, which designated the U.S. and claims priority to FI 20206195 filed Nov. 24, 2020, the entire contents of each of which are hereby incorporated by reference.

FIELD OF THE DISCLOSURE

The disclosure relates to an apparatus and a method for measuring jugular vein pressure "JVP" waveform. The measured jugular vein pressure waveform can be used for example for detecting pulmonary hypertension "PAH".

BACKGROUND

Abnormalities that may occur in a cardiovascular system, if not diagnosed and appropriately treated and/or remedied, may progressively decrease the health of an individual. For example, pulmonary hypertension "PAH" represents in many cases an early indication for an oncoming worsening phase of a heart failure that will take place in average after from three to four weeks from the occurrence of the pulmonary hypertension. In many cases, the pulmonary hypertension can predict the worsening phase of a heart failure in a so early stage that traditional indications of the heart failure such as e.g. increase in weight and increase in blood pressure are typically not present. A heart failure diagnosed at an early phase can often be treated and/or remedied and thereby mortality and a need for hospitalization can decrease significantly.

An examination that concerns behaviour of a jugular vein (lat. vena jugularis) represents a useful tool for diagnosing for example a heart failure. Variation in the jugular vein pressure is produced by changes in a blood flow and pressure in central veins caused by fillings and contractions of the right atrium and the right ventricle of a heart. The jugular vein is directly connected to the right atrium, and this opens a door for a non-invasive examination directed to the right side of the heart i.e. the right ventricle and the right atrium. Publication US2019254542 describes a venous pressure monitoring system which is configured to determine central venous pressure "CVP" based on the jugular vein pressure "JVP". The venous pressure monitoring system described in US2019254542 comprises a signal processor, at least one accelerometer, at least one display, and at least one patch adapted to be held in place or otherwise secured to the neck of an individual. The signal processor is in communication with the at least one accelerometer to compute an estimate for the central venous pressure. An inherent challenge related to the above-described system based on one or more accelerometers is that an output signal of each accelerometer comprises not only a signal component caused by the variation in the jugular vein pressure but also a signal component caused by movements not related to the variation of the jugular vein pressure. The last-mentioned signal component impairs the accuracy of the estimate of the central venous pressure.

Publication Bagyaraj, S., Ragumathulla, M., Vaithiyanathan, D.: Acquisition of Jugular Venous Pulse Waveform by a Non-invasive Technique, Recent advances in mechanical engineering, Lecture notes in mechanical engineering. Springer, Singapore, 25.01.2020 describes a method for measuring a jugular vein pressure "JVP" with the aid of an accelerometer. Publication Baumann, U., Marquis, C., Stoupis, C., Willenberg, T., Takala, J. & Jakob, S.: Estimation on central venous pressure by ultrasound, Resuscitation 64(2), 193-199, Jan. 2, 2005 describes a method for estimating central venous pressure "CVP" with the aid of ultrasound signals.

Publication US2018184977 describes a method for measuring a jugular vein property. The method comprises: coupling a device including an imager to the neck of a patient, imaging the jugular vein at an imaged location using the imager, and analysing at least one image provided by the imager in order to estimate at least one property of the Jugular vein. Publication US2012136240 describes a system for detecting and measuring increased global or local intracranial pressure. The system comprises: devices for performing controlled occlusion of jugular cranial blood outflow and generating occlusion data related to the controlled occlusion, a cranial blood outflow pressure measurement device, and a processor for processing jugular cranial blood outflow occlusion data and cranial blood outflow data to identify and/or measure a functional relationship between the jugular controlled occlusion and the jugular cranial blood outflow pressure. Publication WO2008098353 describes a device for non-invasively measuring at least one parameter of a cardiac blood vessel. The device comprises at least one light source that emits light in the 400 nm to 1000 nm wavelength range, at least one photodetector adapted to receive light from a tissue of a patient in the proximity of the cardiac blood vessel and generate an output based on the received light, and at least one probe for delivering the light from the light source to the tissue of the patient. Publication US2012197118 describes an ultrasonic monitoring device for measuring physiological parameters of a mammal. The ultrasonic monitoring device comprises a substrate, a plurality of ultrasonic transducer elements, a computer readable memory, a microprocessor, and a power source. The ultrasonic transducer elements are coupled to the substrate. Each ultrasonic transducer element is separately configured to transmit a signal to a target area of a mammal and to receive an echo return signal from the target area. Publication WO2018161159 describes a device for measuring the jugular venous pressure of a patient. The device comprises a body defining a longitudinal enclosure and having a window along a length of the longitudinal enclosure to allow light to exit the longitudinal enclosure and a beam generator comprising a moveable portion mounted within the longitudinal enclosure. The beam generator is configured to generate a sheet of light along a plane perpendicular to the longitudinal direction and at an adjustable position along the longitudinal direction and to direct the sheet of light out of the window. The device further comprises an adjustment mechanism for adjusting the position of the moveable portion of the beam generator relative to the body along the longitudinal direction and a readout device indicating the position of the sheet of light along the longitudinal direction. Publication US2010094141 describes a jugular venous pressure "JVP" ruler and a method for its use in measuring jugular venous pressure of a patient. The JVP ruler comprises a transducer configured to detect displacements of a skin of the patient.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In this document, the word "geometric" when used as a prefix means a geometric concept that is not necessarily a part of any physical object. The geometric concept can be for example a geometric point, a straight or curved geometric line, a geometric plane, a non-planar geometric surface, a geometric space, or any other geometric entity that is zero, one, two, or three dimensional.

In accordance with the invention, there is provided a new apparatus for measuring a jugular vein pressure "JVP" waveform. The measured jugular vein pressure waveform can be used for example for detecting pulmonary hypertension "PAH".

An apparatus according to the invention comprises:

a rotation sensor, e.g. a gyroscope, configured to produce a measurement signal indicative of rotation of the rotation sensor when being against a skin of an individual and in a movement sensing relation with a jugular vein of the individual, and a processing system configured to receive the measurement signal and produce a waveform of a motion of the skin in a direction perpendicular to the skin based on the measurement signal, the waveform of the motion of the skin being indicative of the jugular vein pressure waveform.

The rotation sensor is advantageously positioned so that one end of the rotation sensor is nearer to the jugular vein than another end of the rotation sensor. Thus, variation in the jugular vein pressure causes more movement at the first-mentioned end of the rotation sensor than at the last-mentioned end of the rotation sensor, and this difference appears as rotational movement of the rotation sensor. A movement which is not related to the jugular vein pressure and which has a substantially same amplitude and direction over a whole skin area covered by the rotation sensor does not cause a significant rotational movement of the rotation sensor but a translational movement only, and thereby this movement does not cause a significant signal component in the output signal of the rotation sensor. Therefore, the rotation sensor that measures rotation is more insensitive to many movements not related to the variation of the jugular vein pressure than for example an acceleration sensor that measures translational movements.

The pulsation caused by a jugular vein differs from the pulsation caused by a carotid artery due to the difference between the structures of the thin-walled and flexible jugular vein and the thick-walled and muscular carotid artery and also due to different pressures in the jugular vein and in the carotid artery, about 10 mmHg in the jugular vein and about 100 mmHg in the carotid artery. According to experiments, a signal produced by a rotation sensor is more purely a signal produced by a jugular vein whereas a signal produced by an acceleration sensor is a mixture of signals produced by a jugular vein and by a carotid artery. This can be explained based on differences between types of movements measured with a rotation sensor and an acceleration sensor and on differences between types of movements caused by a jugular vein and a carotid artery. A jugular vein causes a local movement on tissue covering the jugular vein whereas a carotid artery causes a sharper pulse that causes a translational movement on a larger area. As mentioned earlier in this document, a movement which is not related to the jugular vein pressure and which has a substantially same amplitude and direction over a larger skin area does not cause a significant rotational movement on a rotation sensor but a translational movement only, and thereby this movement does not cause a significant signal component in the output signal of the rotation sensor. Therefore, the rotation sensor is more insensitive to movements caused by a carotid artery than for example an acceleration sensor that measures translational movements.

An advantage of a rotation sensor with respect to an optical sensor is that an optical sensor can measure only pulsation caused by an outer jugular vein, vena jugularis externa, and thus the optical sensor must be placed accurately to cover the outer jugular vein, which complicates the use of an optical sensor. A rotation sensor measures the pulsation caused mainly by an inner jugular vein, vena jugularis interna, and thus there are no so hard requirements related to positioning than when using an optical sensor.

In accordance with the invention, there is provided a new method for measuring a jugular vein pressure "JVP" waveform. A method according to the invention comprises:

producing a measurement signal with a rotation sensor that is against a skin of an individual and in a movement sensing relation with a jugular vein of the individual, and producing a waveform of a motion of the skin in a direction perpendicular to the skin based on the measurement signal indicative of rotation of the rotation sensor, the waveform of the motion of the skin being indicative of the jugular vein pressure waveform.

Exemplifying and non-limiting embodiments are described in accompanied dependent claims.

Various exemplifying and non-limiting embodiments both as to constructions and to methods of operation, together with additional objects and advantages thereof, will be best understood from the following description of specific exemplifying embodiments when read in conjunction with the accompanying drawings.

The verbs "to comprise" and "to include" are used in this document as open limitations that neither exclude nor require the existence of also un-recited features.

The features recited in the accompanied dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF FIGURES

Exemplifying and non-limiting embodiments and their advantages are explained in greater detail below with reference to the accompanying drawings, in which.

DESCRIPTION OF EXEMPLIFYING AND NON-LIMITING EMBODIMENTS

The specific examples provided in the description below should not be construed as limiting the scope and/or the applicability of the appended claims. Lists and groups of examples provided in the description are not exhaustive unless otherwise explicitly stated.

Figure 1:
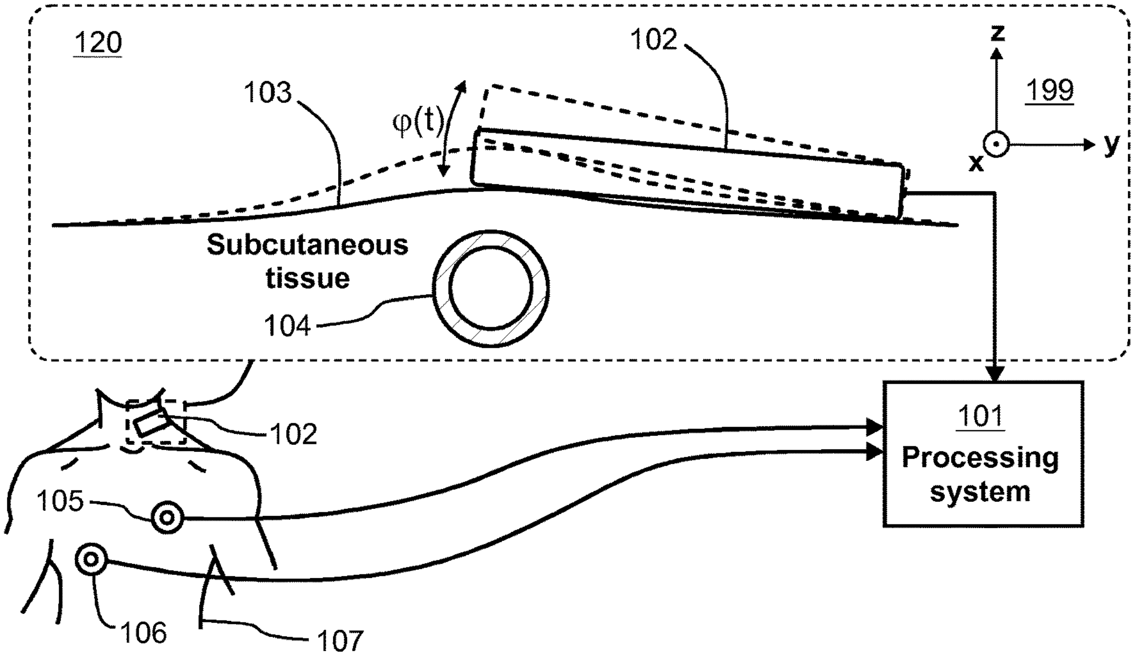
FIG. 1 illustrates an apparatus according to an exemplifying and non-limiting embodiment for measuring a jugular vein pressure "JVP" waveform.

FIG. 1 illustrates an apparatus according to an exemplifying and non-limiting embodiment for measuring a jugular vein pressure "JVP" waveform. The apparatus comprises a rotation sensor 102, e.g. a gyroscope, configured to produce a measurement signal indicative of rotation of the rotation sensor 102 when the rotation sensor 102 is against a skin 103 of an individual 107 and in a movement sensing relation with a jugular vein 104 of the individual. The rotation sensor 102 can be for example a part of a mobile phone that is placed against the skin of the individual 107. The apparatus comprises a processing system 101 configured to receive the measurement signal and to produce a waveform of a motion of the skin 103 in a direction perpendicular to the skin based on the measurement signal. The waveform of the motion of the skin is indicative of the jugular vein pressure "JVP" waveform. In a part 120 of FIG. 1, the direction perpendicular to the skin 103 is substantially parallel with the z-axis of a coordinate system 199. The processing system 101 can be for example a part of a mobile phone. Furthermore, both the processing system 101 and rotation sensor 102 can be for example parts of a same mobile phone. In this exemplifying case, the mobile phone constitutes the apparatus for measuring a jugular vein pressure "JVP" waveform. In the exemplifying case illustrated in FIG. 1, the waveform of the motion of the skin 103 and thereby the jugular vein pressure "JVP" waveform are expressed with temporal variation of a rotation angle φ of the rotation sensor 102. The apparatus may comprise for example a display for presenting the measured jugular vein pressure "JVP" waveform. The display is not shown in FIG. 1. It is also possible that the apparatus comprises a data transfer interface for supplying data expressing the jugular vein pressure "JVP" waveform to an external device. The data transfer interface is not shown in FIG. 1.

In an apparatus according to an exemplifying and non-limiting embodiment, the rotation sensor 102 is configured to measure angular velocity (0 of the rotation sensor 102 and the processing system 101 is configured to compute a time integral of the angular velocity:

$$\varphi(0) = \int_0^T \omega(\tau)d\tau, \tag{1}$$

where the angular velocity ω of the rotation sensor 102 represents the measurement signal and the time integral of the angular velocity, i.e. the angular displacement φ, is indicative of the jugular vein pressure "JVP" waveform.

In an apparatus according to an exemplifying and non-limiting embodiment, the rotation sensor 102 is configured to measure angular acceleration α of the rotation sensor 102 and the processing system 101 is configured to compute a first time integral I1 that is a time integral of the angular acceleration and a second time integral I2 that is a time integral of the first time integral:

$$I1: \omega(T) = \int_0^T \alpha(\tau)d\tau, \tag{2}$$

$$I2: \varphi(T) = \int_0^T \omega(\tau)d\tau, \tag{3}$$

where the angular acceleration α of the rotation sensor 102 represents the measurement signal and the second time integral I2, i.e. the angular displacement φ, is indicative of the jugular vein pressure "JVP" waveform.

The above-mentioned embodiment in which the rotation sensor 102, e.g. a gyroscope, is configured to measure the angular velocity ω is advantageous in the sense that it requires only one integration with respect to time to obtain the waveform of the angular displacement φ of the skin. An integration with respect to time has a low-pass filtering effect and thus it is advantageous if only one integration with respect to time is needed. For example, in a case in which an acceleration sensor is used, it is possible to obtain the waveform of the angular displacement φ with the aid of trigonometric functions but the need for two integrations with respect to time weakens the quality of the measurement and furthermore the need for trigonometric functions complicate the data processing.

In an apparatus according to an exemplifying and non-limiting embodiment, the processing system 101 is configured to receive electric signals from electrodes 105 and 106 on the skin of the individual 107 and the processing system 101 is configured to produce an electrocardiogram "ECG" for a time interval of the jugular vein pressure waveform, i.e. the jugular vein pressure waveform and the electrocardiogram are synchronized with each other.

It is also possible that an apparatus according to an exemplifying and non-limiting embodiment comprises two or more rotation sensors for measuring a same jugular vein in order to improve accuracy. Furthermore, one or more rotation sensors of an apparatus according to an exemplifying and non-limiting embodiment can be one or more implants to be placed under a skin. An implant may utilize the radio frequency identifier "RFID" technology for transferring a measurement signal from the implant to a processing system of the apparatus.

Figure 2A:
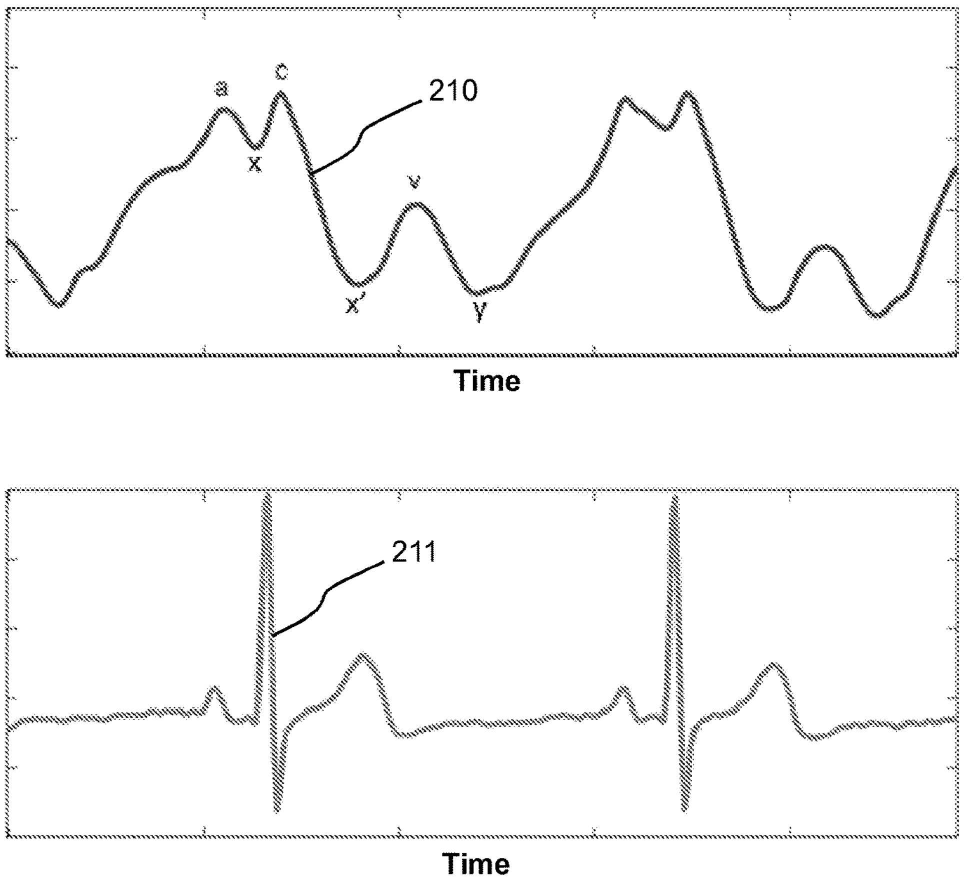
FIG. 2*a* shows exemplifying waveforms produced with an apparatus according to an exemplifying and non-limiting embodiment.

FIG. 2*a* shows an exemplifying jugular vein pressure waveform 210 and an exemplifying electrocardiogram 211 produced with an apparatus according to an exemplifying and non-limiting embodiment. The jugular vein pressure waveform 210 and the electrocardiogram 211 are measured simultaneously.

In an apparatus according to an exemplifying and non-limiting embodiment, the processing system 101 is configured to produce an indicator signal expressing pulmonary hypertension "PAH" in response to a situation in which an a-wave of the jugular vein pressure waveform exceeds a predetermined threshold. The a-wave of the jugular vein pressure waveform 210 is illustrated in FIG. 2*a*. An increase in the a-wave is characteristics to the pulmonary hypertension "PAH" which is caused by increased flow resistance via the pulmonary valve to the pulmonary artery. This is reflected via the right atrium to the jugular vein.

Figure 2B:
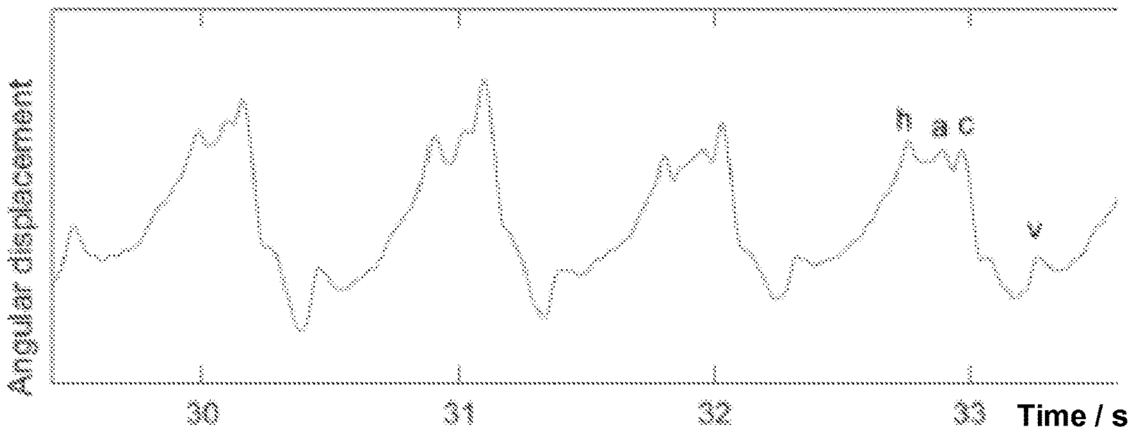
FIG. 2*b* shows an exemplifying waveform of angular displacement produced with an apparatus according to an exemplifying and non-limiting embodiment.
Figure 2C:
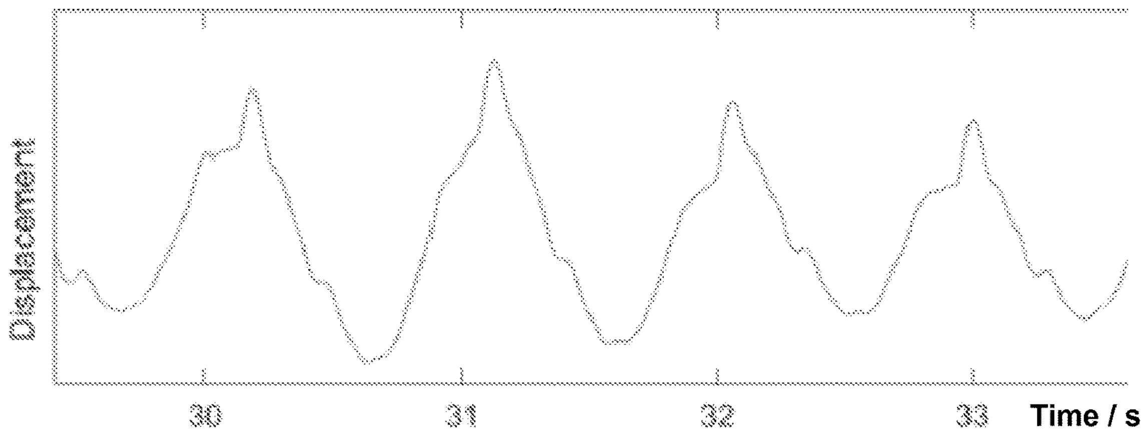
FIG. 2*c* shows a corresponding waveform of displacement produced with an acceleration sensor.

FIG. 2*b* shows an exemplifying waveform of angular displacement produced with an apparatus according to an exemplifying and non-limiting embodiment. In this exemplifying case, the apparatus comprises a gyroscope that is configured to measure the angular velocity and therefore only one integration with respect to time is needed to obtain the waveform of the angular displacement. As shown in FIG. 2*b*, the waveform of the angular displacement obtained with the aid of the gyroscope is able to express the a-, c-, h-, and v-waves. FIG. 2*c* shows a waveform of displacement that has been obtained with two integrations with respect to time based on a signal measured with an acceleration sensor in a direction perpendicular to the skin. As shown in FIG. 2*c*, it is not possible to identify the a-, c-, h-, and v-waves from the waveform obtained with the acceleration sensor.

Figure 3:
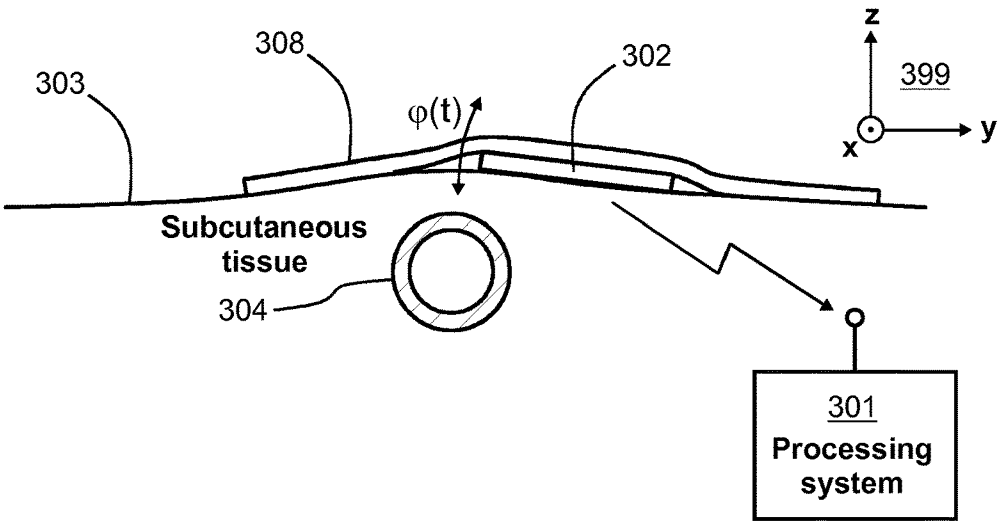
FIG. 3 illustrates an apparatus according to an exemplifying and non-limiting embodiment for measuring a jugular vein pressure "JVP" waveform.

FIG. 3 illustrates an apparatus according to an exemplifying and non-limiting embodiment for measuring a jugular vein pressure "JVP" waveform. The apparatus comprises a rotation sensor 302, e.g. a gyroscope, configured to produce a measurement signal indicative of rotation of the rotation sensor 302 when the rotation sensor 302 is against a skin 303 of an individual and in a movement sensing relation with a jugular vein 304 of the individual. The apparatus comprises a processing system 301 configured to receive the measurement signal and to produce a waveform of a motion of the skin 303 in a direction perpendicular to the skin based on the measurement signal. In FIG. 3, the direction perpendicular to the skin 303 is substantially parallel with the z-axis of a coordinate system 399. The waveform of the motion of the skin is indicative of the jugular vein pressure "JVP" waveform. In the exemplifying case illustrated in FIG. 3, the waveform of the motion of the skin 303 and thereby the jugular vein pressure "JVP" waveform are expressed with temporal variation of a rotation angle φ of the rotation sensor 302.

The exemplifying apparatus illustrated in FIG. 3 comprises a sheet of flexible material 308 that is provided with glue to attach the rotation sensor 302 to the skin 303 of the individual. Thus, the apparatus can be used in different positions of the individual, e.g. when the individual is standing.

In the exemplifying apparatus illustrated in FIG. 3, the processing system 301 and the rotation sensor 302 are configured to maintain a wireless link to transfer the measurement signal from the rotation sensor 302 to the processing system 301. The wireless link can be for example a radio link such as e.g. a Bluetooth® link or a Near Field Communication "NFC" link. It is also possible that the wireless link is an optical or infrared link.

Each of the processing systems 101 and 301 shown in FIGS. 1 and 3 can be implemented for example with one or more processor circuits, each of which can be a programmable processor circuit provided with appropriate software, a dedicated hardware processor such as for example an application specific integrated circuit "ASIC", or a configurable hardware processor such as for example a field programmable gate array "FPGA". Each of the processing systems 101 and 301 may further comprise memory implemented for example with one or more memory circuits each of which can be e.g. a random-access memory "RAM" device.

Figure 4:
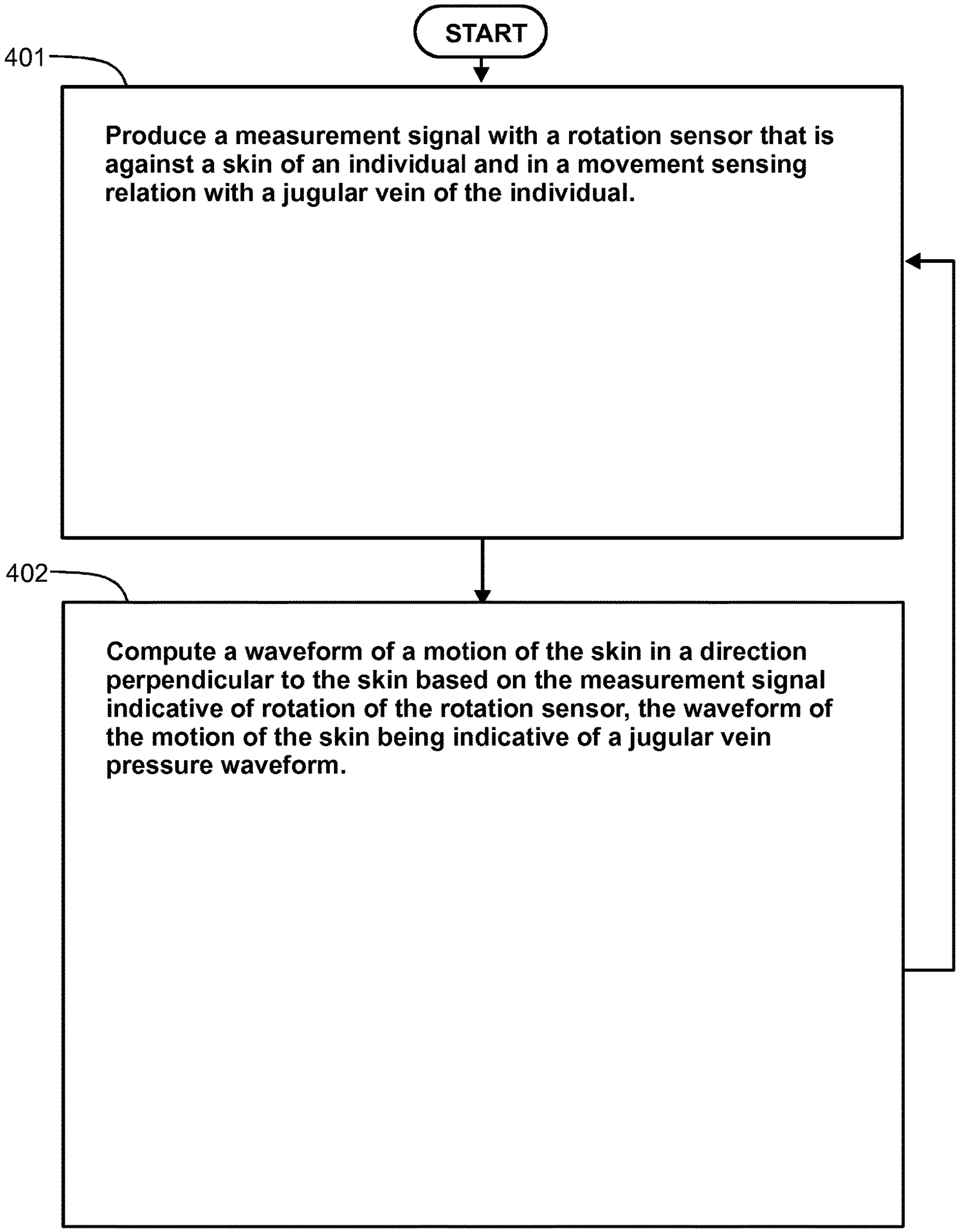
FIG. 4 shows a flowchart of a method according to an exemplifying and non-limiting embodiment for measuring a jugular vein pressure "JVP" waveform.

FIG. 4 shows a flowchart of a method according to an exemplifying and non-limiting embodiment for measuring a jugular vein pressure "JVP" waveform. The method comprises the following actions:

action 401: producing a measurement signal with a rotation sensor that is against a skin of an individual and in a movement sensing relation with a jugular vein of the individual, and action 402: producing a waveform of a motion of the skin in a direction perpendicular to the skin based on the measurement signal indicative of rotation of the rotation sensor, the waveform of the motion of the skin being indicative of the jugular vein pressure waveform.

In a method according to an exemplifying and non-limiting embodiment, the rotation sensor measures angular velocity of the rotation sensor and the method comprises computing a time integral of the measured angular velocity. The measured angular velocity of the rotation sensor represents the above-mentioned measurement signal and the time integral of the measured angular velocity is indicative of the jugular vein pressure waveform.

In a method according to an exemplifying and non-limiting embodiment, the rotation sensor measures angular acceleration of the rotation sensor and the method comprises computing a first time integral that is a time integral of the measured angular acceleration and a second time integral that is a time integral of the first time integral. The measured angular acceleration of the rotation sensor represents the above-mentioned measurement signal and the second time integral is indicative of the jugular vein pressure waveform.

A method according to an exemplifying and non-limiting embodiment comprises receiving one or more electric signals from electrodes on the skin of the individual and producing an electrocardiogram for a time interval of the jugular vein pressure waveform.

In a method according to an exemplifying and non-limiting embodiment, the measurement signal is received from the rotation sensor via a wireless link.

A method according to an exemplifying and non-limiting embodiment comprises producing an indicator signal expressing pulmonary hypertension "PAH" in response to a situation in which an a-wave of the jugular vein pressure waveform exceeds a predetermined threshold.

The specific examples provided in the description given above should not be construed as limiting the scope and/or the applicability of the appended claims. Lists and groups of examples provided in the description given above are not exhaustive unless otherwise explicitly stated. Correspondingly, exemplifying waveforms and other exemplifying results presented above and/or in figures should not be construed as limiting the scope and/or the applicability of the appended claims.

What is claimed is:

1. A system for determining a presence or a risk of a cardiovascular abnormality in an individual, the system comprising:

(a) a rotation sensor configured to generate a motion signal when being against a skin of an individual and in a movement sensing relation with a jugular vein of the individual; and (b) one or more processors, wherein i) the motion signal is angular velocity of the rotation sensor and the one or more processors is/are configured to compute an angular displacement of the rotation sensor as a time integral of the angular velocity, or ii) the motion signal is angular acceleration of the rotation sensor and the one or more processors is/are configured to compute a first time integral of the angular acceleration and the angular displacement of the rotation sensor as a second time integral of the first time integral, and wherein the one or more processors is/are configured to detect an a-wave of a waveform of the angular displacement of the rotation sensor, compare the a-wave of the waveform of the angular displacement of the rotation sensor to a predetermined threshold, and produce an indicator signal expressing the cardiovascular abnormality in response to a situation in which the a-wave of the waveform of the angular displacement of the rotation sensor exceeds the predetermined threshold.

2. The system of claim 1, wherein the one or more processors are further configured to determine a presence or a risk of a cardiovascular disorder based at least in part on determination of the presence or the risk of the cardiovascular abnormality.

3. The system of claim 1, wherein the cardiovascular abnormality comprises pulmonary artery hypertension (PAH) or heart failure (HF).

4. The system of claim 1, further comprising one or more electrodes configured to be in contact with the skin area of the individual to generate an electrocardiogram (ECG) signal.

5. The system of claim 4, wherein the one or more processors are further configured to map the ECG signal to at least a portion of a jugular vein pressure pattern represented by the angular displacement of the rotation sensor.

6. The system of claim 5, wherein the one or more processors are further configured to determine the presence of the risk of the cardiac abnormality of the individual based at least in part on the mapped ECG signal and the at least portion of the jugular vein pressure pattern.

7. The system of claim 1, wherein the rotation sensor comprises an inertial sensor suitable for being in contact with a body surface of the individual.

8. The system of claim 7, wherein the inertial sensor comprises one or more of: a gyroscope, or an inertial measurement unit, or any combination thereof.

9. The system of claim 1, further comprising a wearable patch or a handheld device comprising the rotation sensor.

10. The system of claim 9, wherein the handheld device comprises a mobile phone.

11. A computer-implemented method for determining a presence or a risk of a cardiovascular abnormality, the method comprising generating, with a rotation sensor, a motion signal when the rotation sensor is against a skin of an individual and in a movement sensing relation with a jugular vein of the individual, wherein i) the motion signal is angular velocity of the rotation sensor and the method comprises computing an angular displacement of the rotation sensor as a time integral of the angular velocity, or ii) the motion signal is angular acceleration of the rotation sensor and the method comprises computing a first time integral of the angular acceleration and then computing the angular displacement of the rotation sensor as a second time integral of the first time integral, and wherein the method comprises detecting an a-wave of a waveform of the angular displacement of the rotation sensor, comparing the a-wave of the waveform of the angular displacement of rotation sensor to a predetermined threshold, and producing an indicator signal expressing the cardiovascular abnormality in response to a situation in which the a-wave of the waveform of the angular displacement of the rotation sensor exceeds the predetermined threshold.

12. The computer-implemented method of claim 11, wherein the rotation sensor comprises an inertial sensor in contact with a body surface of the individual.

13. The computer-implemented method of claim 12, wherein the inertial sensor comprises one or more of: a gyroscope, or an inertial measurement unit, or any combination thereof.

14. The computer-implemented method of claim 11, further comprising mapping an ECG signal pertaining to the individual to at least a portion of a jugular vein pressure pattern represented by the angular displacement of the rotation sensor.

15. The computer-implemented method of claim 14, further comprising determining the presence or the risk of the cardiac abnormality of the individual based at least in part on the mapped ECG signal and the at least portion of the jugular vein pressure pattern.

16. The computer-implemented method of claim 11, further comprising determining a presence or a risk of a cardiovascular disorder based at least in part on determination of the presence or the risk of the cardiovascular abnormality.

17. The computer-implemented method of claim 11, wherein the cardiovascular abnormality comprises pulmonary artery hypertension (PAH) or heart failure (HF).

* * * * *